United States Patent [19]

Tamagawa et al.

[11] Patent Number: 4,522,493
[45] Date of Patent: Jun. 11, 1985

[54] PARTIAL INJECTION APPARATUS

[75] Inventors: Akira Tamagawa, Hino; Tokio Kano, Kunitachi, both of Japan

[73] Assignee: Olympus Optical Co., Ltd., Japan

[21] Appl. No.: 436,662

[22] Filed: Oct. 26, 1982

[30] Foreign Application Priority Data

Nov. 19, 1981 [JP] Japan .................................. 56-184371

[51] Int. Cl.³ ......................... G01N 1/14; G01N 33/48
[52] U.S. Cl. ...................................... 356/36; 250/564; 356/39
[58] Field of Search .................... 356/39, 36; 250/574, 250/576, 564, 565

[56] References Cited

U.S. PATENT DOCUMENTS

| 3,912,393 | 10/1975 | Hossom et al. | 250/574 X |
| 4,129,381 | 12/1978 | Wied et al. | 356/36 |
| 4,168,294 | 9/1979 | Calzi et al. | 356/440 X |

Primary Examiner—Vincent P. McGraw
Attorney, Agent, or Firm—Ostrolenk, Faber, Gerb & Soffen

[57] ABSTRACT

A partial injection apparatus is adapted to partially inject a required amount of a sample and to control an amount of a diluent to be added therein by partially injecting while detecting concentration of a test fluid which contains the required amount of the sample and the diluent added in the sample so that a desired concentration of the test fluid can be obtained.

8 Claims, 1 Drawing Figure

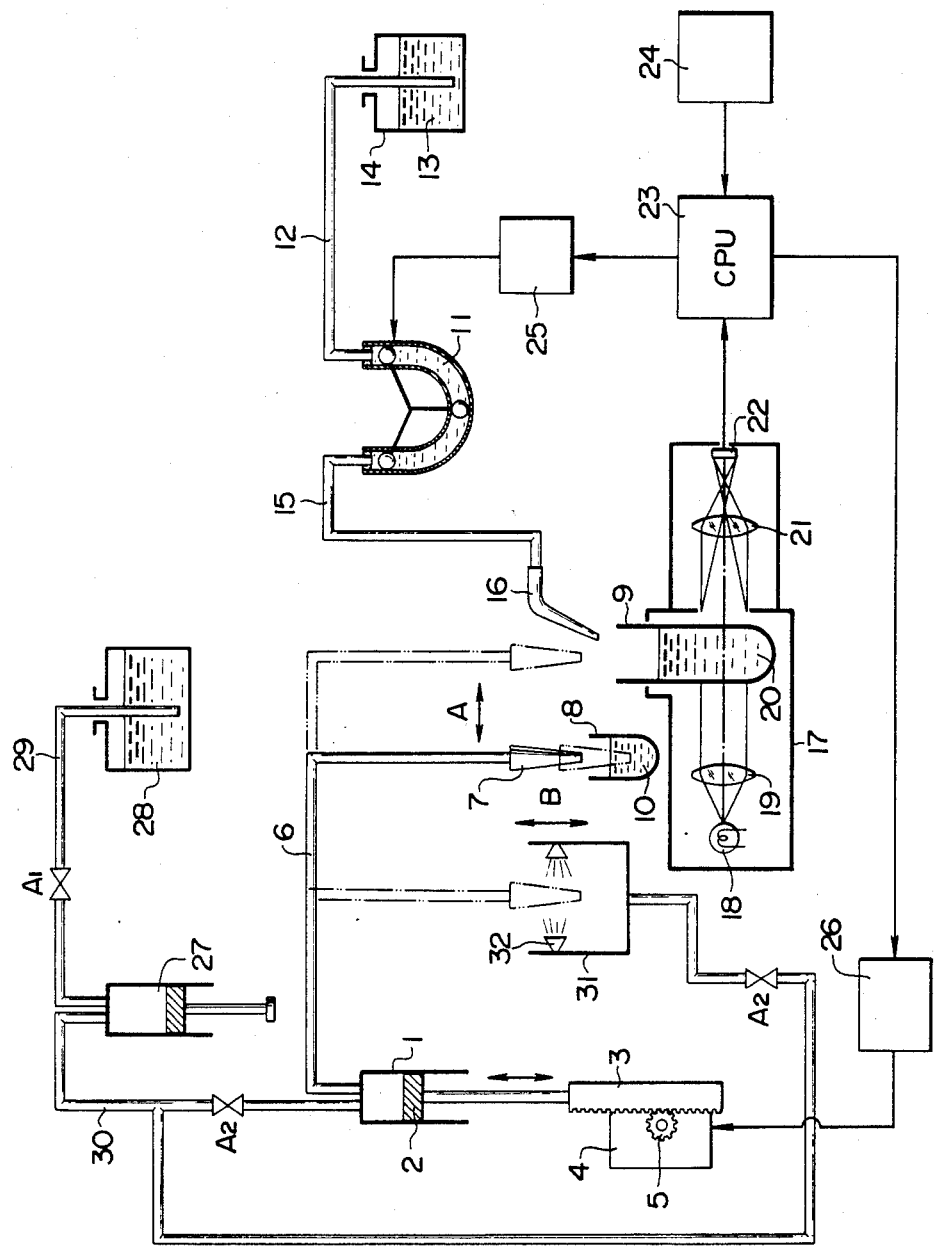

PARTIAL INJECTION APPARATUS

BACKGROUND OF THE INVENTION

The present invention relates to a partial injection apparatus, and more particularly, to such apparatus for obtaining a predetermined concentration of a test fluid to be obtained by adding a diluent to a sample or the like.

By way of example, in the field of a blood analysis, a blood corpuscle floating fluid to be used for either a reagent or a sample will be prepared by aspirating and ejecting either a blood corpuscle floating fluid of a desired concentration with a pipet or a blood corpuscle sample with a partial injector resorting to operations only for directly aspirating and ejecting a fluid of a desired amount.

However, in case of mixing the blood corpuscle sample and its diluent in a given volumetric ratio using either a pipet or a partial injector, the blood corpuscle sample being aspirated adheres to the inner wall thereof in a large amount, disadvantageously resulting in a decrease of the ejected amount compared with the amount aspirated and also resulting in a variation in the amount ejected. Thus, as a practical matter, a blood corpuscle floating fluid prepared with either the pipet or the partial injector will have a concentration which is lower than a desired value with the result that a precise analysis may not be performed. When a blood corpuscle floating fluid having the lower concentration has been prepared, the following measures should be taken to make it a desired concentration. Namely, by applying a centrifugation operation (for example, for five minutes at 3000 rpm) to the floating fluid, a designated amount of its supernatant fluid may be skimmed. Then the desired concentration must be obtained by agitating the remaining fluid again. These operations are troublesome and time consuming. On the other hand, it may be desirable to raise the concentration of the floating fluid by partially injecting an increment of the sample. It is impossible, however, to obtain precisely a desired concentration of the floating fluid since a partial injecting operation of an infinitesimal amount of the sample can not be effected precisely.

SUMMARY OF THE INVENTION

It is an object of the invention to provide a partial injection apparatus which eliminates the foregoing disadvantages and is adapted to prepare a test fluid of a desired concentration by a simple operation.

The partial injection apparatus according to the invention is characterized by the provision of means for partially injecting a sample into a container, means for partially injecting a diluent into the container, means for detecting a concentration of the test fluid consisting of the sample and the diluent within the container and means for controlling said means for partially injecting the sample and said means for partially injecting the diluent so as to obtain a desired concentration of the test fluid in accordance with the concentration detected by said detecting means.

According to the present invention, the partial injection apparatus first partially injects a sample and a diluent, next measures a concentration of a test fluid thus obtained, and then partially injects an increment of the diluent. Accordingly, it has the following advantages:

(1) even though the concentration of the test fluid is inaccurate since an indefinite amount of the sample will adhere to the nozzle which partially injects the sample, a test fluid of a precise concentration can be obtained by partially adding an increment of a diluent in accordance with the sample injected into a measuring tube to secure a given concentration, thus improving the accuracy of the analysis using the test fluid thus obtained;

(2) a required amount of the test fluid can be prepared in a short time so as to minimize changes resulting from the standing of the sample or the like, thus permitting a high accuracy in a result of the analysis employing the prepared test fluid to be achieved; and (3) as it features extremely simple and reliable use, an erroneous operation by an operator can be avoided.

BRIEF DESCRIPTION OF THE DRAWING

The single FIGURE is a diagram illustrating an example of the construction of a partial injection apparatus according to the invention.

DESCRIPTION OF THE PREFERRED EMBODIMENT

In the FIGURE, a syringe 1 which acts as a partial injector for a sample has a piston 2 to which a rack 3 is connected. The rack 3 meshes with a pinion 5 which is driven by a motor 4. The syringe 1 is connected through a tube 6 to a nozzle 7. The tube 6 and the nozzle 7 are movable over and among a sample tube 8, a measuring tube 9 and a cleaning tank 31 in the direction of arrow A and are also movable up and down in the direction of arrow B over the sample tube 8 and the cleaning tank 31 by means of a nozzle transfer mechanism (not shown) so that the end of the nozzle 7 can be immersed in the blood corpuscle sample 10 contained within the sample tube 8.

A pump 11 acts as a partial injector for a diluent, one end of which is connected to a tube 12. The tube 12 is immersed in the diluent 13 contained within a diluent tank 14. The other end of the pump 11 is connected through a tube 15 to a nozzle 16 which is located over the measuring tube 9 so as to eject the diluent 13 thereinto.

The measuring tube 9 is disposed within a measuring chamber 17 in such a manner that light flux emitted from a light source 18 can be transmitted through a lens 19 and a test fluid 20 contained within the measuring tube 9. A concentration of the test fluid 20 can be measured by receiving the transmitted light flux with a photoelectric transducer element 22 through a lens 21. The transducer element 22 is formed with, for example, SBC (silicon blue cell), the output of which is supplied to a central processing unit 23 (hereinafter abbreviated to as CPU). The CPU 23 is connected to a keyboard 24 into which information as to a desired concentration and a required amount of the test fluid is entered. The CPU 23 is connected to a pump drive circuit 25 which drives the pump 11 as well as a motor drive circuit 26 which drives the motor 4. A pulse motor may be preferably used in place of a drive motor for the pump 11 so as to precisely control a rotational angle thereof.

It will be seen that the nozzle 7 must be cleaned since a sample adheres thereto when aspirated and a subsequent aspiration of another sample may cause contamination of the resulting sample. To this end, a tank 28 for containing cleaning liquid is provided so that the cleaning liquid can be aspirated through a tube 29 and an electromagnetic valve $A_1$ by a cleaning pump 27 and further can be led through a tube 30 and two electromagnetic valves A₂, A₂ to a nozzle cleaning tank 31. The cleaning tank 31 has a plurality of injection nozzles 32 for the cleaning liquid on its periphery.

In operation, a required amount and a desired concentration of a test fluid to be prepared are inputted into the CPU 23 by means of the keyboard 24. First the end of the nozzle 7 is immersed into the blood corpuscle sample 10 within the sample tube 8 and then the rack 3 is driven a given distance by rotating the motor 4 with the motor drive circuit 26 in accordance with the concentration of the test fluid which is inputted into the CPU 23, thus resulting in suction of the blood corpuscle sample 10 of a given amount by the syringe 1. Next the nozzle 7, after being lifted from the sample tube 8, is moved to the topside of the measuring tube 9 and then a given amount of the blood corpuscle 10 which has been sucked by the syringe 1 is injected into the measuring tube 9. Then a diluent 13 is injected into the measuring tube 9 in succession with activation of the pump drive circuit 25 by the CPU 23. The blood corpuscle sample is diluted by a diluent within the measuring tube 9 and a concentration value of the corpuscle sample is obtained in the form of a voltage derived by the transducer element 22 on which light from the source 18 impinges after having been transmitted through the test fluid. The derived voltage is delivered to the CPU 23 which has stored the desired concentration value as a voltage into which the desired concentration value is converted as shown in Table 1. When the voltage derived by the transducer element 22 reaches the stored voltage, the pump drive circuit 25 is made inoperative to automatically stop the pump.

TABLE 1

|  | 0 | 1 | 2 | 3 | ... | 28 | 29 | 30 |
|---|---|---|---|---|---|---|---|---|
| Voltage mV | 80 | 75 | 72 | 70 | ... | 19 | 17 | 15 |
| Concentration % | 1.0 | 1.1 | 1.2 | 1.3 | ... | 3.8 | 3.9 | 4.0 |

Thus, it is possible to obtain a test fluid 20 of the desired concentration within the measuring tube 9.

To clean the nozzle 7 after the sample has been partially ejected into measuring tube 9, the nozzle 7 is moved in the cleaning tank 31 by the nozzle transfer mechanism (not shown). First, a cleaning liquid in the cleaning liquid tank 28 is aspirated with activation of the pump 27 by opening the electromagnetic valve A₁. Subsequently, upon closing the valve A₁ and opening the valves A₂, A₂, the inside of the nozzle 7 is cleaned by ejecting the cleaning liquid upon activation of the pump 27 and simultaneously the outside thereof is cleaned with ejection from the ejecting nozzle 32 which is provided within the cleaning tank 31.

It should be understood that the construction of the cleaning pump and tubing system as described above is not restricted thereto.

According to the partial injection apparatus of the embodiment, a test fluid of a desired concentration can be also obtained by the following alternative operation. The alternative operation is the same as that described above with respect to the steps for entering a required amount and a desired concentration of a test fluid into the CPU 23 and ejecting a given blood corpuscle sample into the measuring tube 9 in accordance with the entered value. Subsequently, a diluent 13 corresponding to a portion of the required amount of diluent, for example, one half, of a test fluid to be prepared is ejected into the measuring tube 9 utilizing the pump drive circuit 25 and a voltage derived by the transducer element 22 on which light from the source 18 impinges which is transmitted through the test fluid is delivered to the CPU 23. It is presently assumed that the ejected amount of the sample is negligibly small to the amount of the diluent. The CPU 23 adopts a concentration value corresponding to a voltage in Table 1 which is closest to the measured voltage. Assuming that the concentration thus derived is x, the amount of the diluent ejected into the measuring tube 9 is y and a desired concentration of the test fluid to be prepared is z, an increment of the diluent to be additionally injected is expressed as $(x/y)\cdot y - y$. Accordingly, if the pump 11 is controlled by the drive circuit 25 so that the diluent of an increment derived from the expression can be ejected, a desired concentration of the test fluid within the measuring tube can be obtained and the total amount of the test fluid is extremely close to a desired value.

What is claimed is:

1. A partial injection apparatus, comprising:
   (A) sample injection means for injecting approximately a predetermined amount of sample into a container, said sample injection means including:
      (1) a sample tube containing a sample to be diluted;
      (2) a nozzle;
      (3) a cleaning tank for applying a cleaning fluid to said nozzle when said nozzle is located in said cleaning tank; and
      (4) operating means for moving said nozzle into said sample tube, aspirating a predetermined amount of said sample into said nozzle, moving said nozzle into said container and injecting substantially all of said sample into said container, and thereafter moving said nozzle into said cleaning tank;
   (B) diluent injecting means for injecting, under the control of a control means, a diluent into said container so as to form a test fluid in said container, said test fluid including said sample and said diluent;
   (C) detecting means for detecting the concentration of said test fluid; and
   (D) said control means causing said diluent injecting means to:
      (1) inject a first predetermined amount of diluent into said container, while amount is independent of the actual amount of fluid in said container, so that after said sample and said predetermined amount of diluent has been injected into said container the concentration of test fluid in said container will be at a level less than a desired level; and thereafter
      (2) injecting an additional amount of diluent into said container as a function of said detected concentration so as to bring the concentration of said test fluid to said desired level.

2. A partial injection apparatus according to claim 1, in which said operating means comprises a syringe coupled to said nozzle and piston for aspirating and injecting said sample, and a drive mechanism for driving said piston.

3. A partial injection apparatus according to claim 1, in which said diluent injection means comprises a diluent tank for holding a diluent, a second nozzle, one or more tubes connecting said tank to said second nozzle and a pump for aspirating the diluent from the diluent tank, passing it through said one or more tubes, and ejecting said diluent through said second nozzle.

4. A partial injection apparatus according to claim 1, in which said container comprises a measuring tube for holding said test fluid, said measuring tube permitting an optical measurement of the test fluid therein by transmitted light.

5. A partial injection apparatus according to claim 1, in which the detecting means comprises a light source, an optical system for passing light rays radiated from said light source through said test fluid and a photoelectric transducer element for receiving said light rays transmitted through said test fluid.

6. A partial injection apparatus according to claim 1, in which said control means comprises a keyboard for entering a desired concentration of test fluid, a central processing unit for comparing the actual concentration of the test fluid as indicated by said detecting means to said desired level and drive circuits for controlling said diluent injecting means to cause the concentration of said test fluid to reach said desired level.

7. A partial injection apparatus according to claim 1, wherein said control means determines said additional amount of diluent to be injected into said container as a function of said detected concentration prior to the time said additional amount of diluent is injected into said container.

8. A partial injection apparatus according to claim 1, wherein said cleaning tank includes means for spraying cleaning fluid into said cleaning tank when said nozzle is located in said cleaning tank.

* * * * *